(12) United States Patent
Best et al.

(10) Patent No.: US 10,799,231 B2
(45) Date of Patent: Oct. 13, 2020

(54) SUTURE-IMPLANT CONSTRUCT AND METHOD OF DEPLOYING THE SAME

(71) Applicant: Arthrex, Inc., Naples, FL (US)

(72) Inventors: Joshua J. Best, Naples, FL (US); Andrew Osika, Naples, FL (US); Kenneth T. Helenbolt, Naples, FL (US)

(73) Assignee: Arthrex, Inc., Naples, FL (US)

( * ) Notice: Subject to any disclaimer, the term of this patent is extended or adjusted under 35 U.S.C. 154(b) by 367 days.

(21) Appl. No.: 15/864,948

(22) Filed: Jan. 8, 2018

(65) Prior Publication Data

US 2019/0209156 A1 Jul. 11, 2019

(51) Int. Cl.
*A61B 17/04* (2006.01)
*A61B 17/06* (2006.01)
*A61B 17/00* (2006.01)

(52) U.S. Cl.
CPC .... *A61B 17/0401* (2013.01); *A61B 17/06166* (2013.01); *A61B 2017/00407* (2013.01); *A61B 2017/0406* (2013.01); *A61B 2017/0409* (2013.01); *A61B 2017/0445* (2013.01); *A61B 2017/0464* (2013.01); *A61B 2017/0496* (2013.01); *A61B 2017/06176* (2013.01)

(58) Field of Classification Search
CPC ..... A61B 17/04; A61B 17/06; A61B 17/0401; A61B 17/06166; A61B 2017/0496; A61B 2017/0445; A61B 2017/0464; A61B 2017/0409; A61B 2017/0414
See application file for complete search history.

(56) References Cited

U.S. PATENT DOCUMENTS

| | | | |
|---|---|---|---|
| 6,972,027 B2 | 12/2005 | Fallin et al. | |
| 8,273,106 B2 * | 9/2012 | Stone | A61B 17/0401 606/232 |
| 8,828,054 B2 | 9/2014 | Caborn et al. | |
| 8,961,538 B2 | 2/2015 | Koogle, Jr. et al. | |
| 2006/0190042 A1 | 8/2006 | Stone et al. | |
| 2008/0140092 A1 | 6/2008 | Stone et al. | |
| 2008/0140093 A1 | 6/2008 | Stone et al. | |
| 2010/0211097 A1* | 8/2010 | Hadba | B21G 7/02 606/232 |
| 2015/0066058 A1 | 3/2015 | Caborn et al. | |
| 2015/0066061 A1 | 3/2015 | Caborn et al. | |
| 2015/0142052 A1 | 5/2015 | Koogle, Jr. et al. | |

FOREIGN PATENT DOCUMENTS

WO WO 2006/086275 A2 8/2006
WO WO 2016/068896 A1 5/2016

OTHER PUBLICATIONS

AS Meniscal™ Repair Device Technique Guide, Covidien, 2012.
CrossFix® II Meniscal Repair System, Cayenne Medical, 2011.
Keith Lawhorn, M.D., MaxFire MarXmen Meniscal Repair Device, Biomet Sports Medicine, 2007.

(Continued)

*Primary Examiner* — Vi X Nguyen
(74) *Attorney, Agent, or Firm* — Blank Rome LLP (57) ABSTRACT

This disclosure relates to suture-implant constructs, surgical devices configured to deliver suture-implant constructs, and methods of repairing damaged tissue.

16 Claims, 8 Drawing Sheets

(56) References Cited

OTHER PUBLICATIONS

Omnispan Meniscal Repair utilizing the Chia Percpasser Suture Passer, Omnispan, 2010.
Q-Fix All-Suture Implant, Smith & Nephew, 2015.
Charles H. Brown, Jr., MD et al., Fast-Fix 360 Meniscal Repair System All-Inside Meniscal Repair, Smith & Nephew, 2010.
SpeedCinch Meniscal Repair, Arthrex, 2016.
Knee Preservation System, Sequential Meniscal Running Stich Surgical Technique, ConMed Linvatec, 2014.

* cited by examiner

SUTURE-IMPLANT CONSTRUCT AND METHOD OF DEPLOYING THE SAME

BACKGROUND

This disclosure relates to a suture-implant construct, a surgical device configured to deliver the suture-implant construct, and a method for repairing damaged tissue. Orthopedic procedures are often performed to repair musculoskeletal injuries, such as those sustained during sporting activities. Tears in the meniscus are known to be repaired by deploying implants on either side of the tear, tensioning suture between the implants to close the tear, and allowing it to heal.

SUMMARY

This disclosure relates to suture-implant constructs including one or more sheaths and a flexible strand, such as a strand of suture, suture tape, and the like. The disclosure also relates to surgical devices configured to deliver the suture-implant constructs and methods of repairing damaged tissue. An exemplary suture-implant construct includes a strand of suture and one or more sheaths arranged to provide a plurality of spaced-apart anchor portions. When used to repair a tear in a meniscus, for example, the disclosed arrangement resists "tear-through".

A suture-implant construct includes, inter alia, a strand of suture and one or more sheaths and each sheath comprising a plurality of spaced-apart anchor portions.

A surgical device includes, inter alia, a cannula, and a suture-implant construct comprising a strand of suture and one or more sheaths, and each sheath comprising a plurality of anchor portions. A first anchor portion can be in a deploy position with respect to the cannula and a second anchor portion can be in a standby position proximal to the first anchor portion. A surgical device can further include a pusher moveable within the cannula to deploy the first anchor portion and to move the second anchor from the standby position to a deploy position.

A method includes, inter alia, moving a pusher of a surgical device in a distal direction to deploy a first anchor portion of a suture-implant construct out of a cannula and to move a second anchor portion of the suture-implant construct distally within the cannula. The suture-implant construct has a strand of suture and one or more sheaths, and each sheath comprising a plurality of anchor portions. A method can further include moving the pusher in a proximal direction and subsequently moving the pusher in the distal direction again to deploy the second anchor portion out of the cannula.

DETAILED DESCRIPTION

This disclosure generally relates to surgical devices and methods for using the same, such as is disclosed in commonly assigned U.S. patent application Ser. No. 15/643,520, entitled Surgical Device and Methods of Delivering Implants, filed on Jul. 7, 2017, the subject matter of which is herein incorporated by reference. This disclosure relates to suture-implant constructs including one or more sheaths and a flexible strand, such as a strand of suture, suture tape, or the like. The disclosure also relates to surgical devices configured to deliver the suture-implant constructs as disclosed herein and methods of repairing damaged tissue. An exemplary suture-implant construct includes a strand of suture and one or more sheaths, and each sheath comprises at least a first anchor portion and a second anchor portion spaced-apart from the first anchor portion. When used to repair a tear in a meniscus, for example, the disclosed arrangement resists "tear-through".

A suture-implant construct includes, inter alia, a strand of suture and one or more sheaths each arranged to provide a plurality of spaced-apart anchor portions.

In a further embodiment, each sheath has a first end and a second end, the first anchor portion is adjacent the first end of the sheath, and the second anchor portion is adjacent the second end of the sheath.

In a further embodiment, the strand of suture passes through a bore of the sheath between the first and second ends thereof.

In a further embodiment, each sheath has an increased width dimension between the first and second anchor portions.

In a further embodiment, the first anchor portion includes at least one splice point in which the strand of suture exits and re-enters the bore, and the second anchor portion includes at least one splice point in which the strand of suture exits and re-enters the bore.

In a further embodiment, the first anchor portion includes two splice points spaced-apart from one another, and the second anchor portion includes two splice points spaced-apart from one another.

In a further embodiment, an end of the strand of suture is looped-over and affixed to the strand of suture adjacent one of the two splice points of the first anchor portion.

In a further embodiment, the strand of suture includes a bulb adjacent the first end of the sheath.

In a further embodiment, the strand of suture is a mono-filament suture including barbs.

In a further embodiment, the sheath is a tubular sleeve made of a flexible material, such as polyester suture material or the like.

A surgical device includes, inter alia, a cannula, and a suture-implant construct comprising a strand of suture and at least one sheath comprising at least a first anchor portion and a second anchor portion. The first anchor portion can be in a deploy position with respect to the cannula and the second anchor portion can be in a standby position proximal to the first anchor portion. In an embodiment, third, fourth, fifth, etc. anchor portions of the sheath can be in a standby position. A surgical device can further include a pusher moveable within the cannula to deploy the first anchor portion and to move any subsequent anchor portions from the standby position to the deploy position.

In a further embodiment, the pusher includes a shuttling rack in contact with the second anchor portion of the sheath when the second anchor portion is in the standby position. Where the shuttling rack can be tubular or rectangular. In one embodiment, the shuttling rack includes a plurality of barbs.

In a further embodiment, the pusher is a holder tube that extends through and moves freely with respect to the sheath.

In a further embodiment, the sheath has a first end and a second end, the first anchor portion is adjacent the first end of the sheath, the second or subsequent anchor portion is adjacent to the second end of the sheath, the strand of suture passes through a bore of the sheath between the first and second ends, and the sheath has an increased width dimension between the plurality of anchor portions.

A method according to an exemplary aspect of the present disclosure includes, inter alia, moving a pusher of a surgical device in a distal direction to deploy a first anchor portion of a suture-implant construct out of a cannula and to move at least a second anchor portion of the suture-implant construct distally within the cannula. The suture-implant construct can have a strand of suture and one or more sheaths arranged to provide a plurality of anchor portions. A method can further include moving a pusher in a proximal direction and subsequently moving the pusher in the distal direction again to deploy the second anchor portion out of the cannula.

In a further embodiment, the anchor portions are implanted into a meniscus to repair a tear in the meniscus.

In a further embodiment, a method includes tensioning the strand of suture to close the tissue repair, such as a meniscal tear.

In a further embodiment, the anchor portions are implanted through a surface of the torn meniscus to outside the knee capsule. The sheath can also cover the strand of suture between the anchor portions and extend along the surface of the meniscus. In a further embodiment, the sheath has an increased width dimension on the surface of the meniscus.

Figure 1:
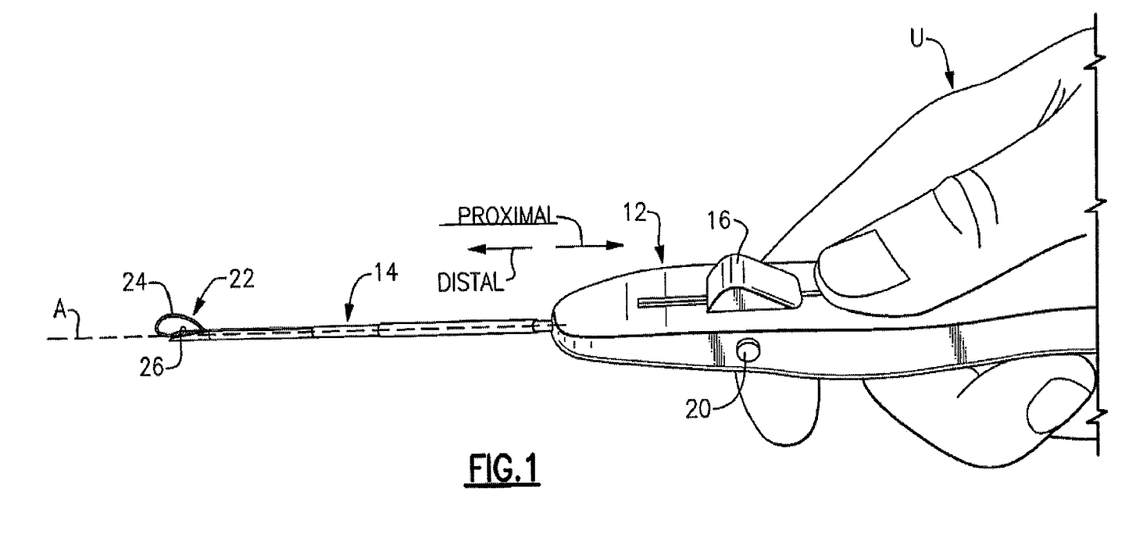
FIG. 1 illustrates an example surgical device held by a user, such as a surgeon.

FIG. 1 illustrates an example surgical device 10. The surgical device 10 includes a handle 12 and a cannula 14 projecting distally (the "distal" direction is labeled in various figures for reference) from the handle 12 along a longitudinal axis A. The handle 12 includes a trigger 16, which in this example is a thumb trigger. The trigger 16 is moveable in the distal and proximal directions (the "proximal" direction is labeled in various figures reference) to move a pusher 18 (FIG. 2), which itself is moveable within the cannula 14 in the distal and proximal directions.

In one example, the handle 12 may include a spring or other biasing element configured to bias the trigger 16 in the proximal direction. In order to move the trigger 16 in the distal direction, a user U (i.e., a surgeon) uses their thumb, for example, to apply a force to the trigger 16 sufficient to overcome the bias of the spring such that the trigger 16 slides distally. When the user U releases their thumb, the trigger 16 moves proximally back to a resting position under the bias of the spring or other biasing element.

The handle 12 may optionally incorporate a brake. In this example, the brake is selectively activated by depressing a button 20 disposed on an exterior surface of the handle 12. When the button 20 is depressed, the brake engages the trigger 16, or a structure associated with the trigger 16, to hold the trigger 16 in place and overcome the proximal bias of the trigger 16. This braking function is useful in some circumstances, such as when penetrating a meniscus with the cannula 14, for example.

The cannula 14 is configured to penetrate soft tissue within the body. To this end, a distal-most tip of the cannula 14 is relatively sharp and may be tapered or pointed in some examples. Further, the cannula 14 is loaded with a suture-implant construct 22 (sometimes referred to as a "suture construct"), which includes a strand of suture 24 and at least one sheath 26. A user can position the cannula 14 adjacent a meniscus tear, for example, and use the trigger 16 to selectively deploy the suture-implant construct 22.

Figures 2, 3:
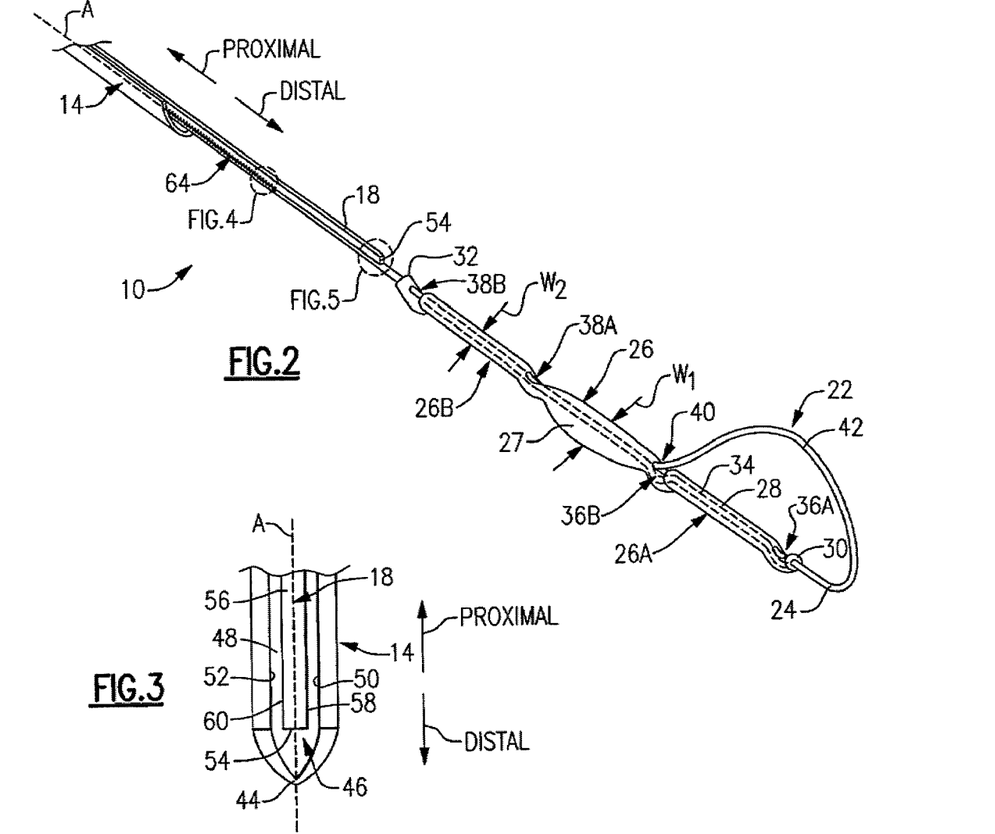
FIG. 2 is a perspective view of the surgical device of FIG. 1 with a suture-implant construct and a pusher partially removed from the surgical device for purposes of illustration.
FIG. 3 is a top view of a distal end of the surgical device, and illustrates the arrangement between a cannula and the pusher.

FIG. 2 illustrates a distal end of the surgical device 10 with the pusher 18 and suture-implant construct 22 partially removed from the cannula 14 for ease of reference. In this example, the strand of suture 24 and the sheath 26 are arranged to provide the suture-implant construct 22 with a first anchor portion 26A and a second anchor portion 26B. As shown, the sheath 26 includes a distal end 30 and a proximal end 32. The first anchor portion 26A is adjacent the distal end and is distal of the second anchor portion 26B. The second anchor portion 26B is adjacent the proximal end 32 and is proximal of the first anchor portion 26A. In an embodiment, the sheath 26 and its anchor portions 26A and 26B are one-piece.

It should be understood that while two anchor portions 26A, 26B are illustrated, the sheath may include additional anchor portions. In one particular example, the strand of suture 24 and the sheath 26 are arranged to provide the suture-implant construct with four anchor portions arranged sequentially along the strand of suture 24. In an embodiment, the four anchor portions are space-apart from one another.

The sheath 26 has a substantially tubular body that extends between the distal and proximal ends 30, 32. In this example, the sheath 26 is provided by a single, integrated body. The sheath 26 further includes a bore 34 (illustrated in phantom) communicating with the distal and proximal ends 30, 32 for accommodating the strand of suture 24. The strand of suture 24 is flexible and is passed through the bore 34. In the illustrated examples, the strand of suture 24 is encased by the sheath 26 throughout substantially the entire length of the sheath 26, with the exception of a plurality of splice points.

Each of the first and second anchor portions 26A, 26B includes at least one splice point, in which the strand of suture 24 exits and re-enters the bore 34. In this example, the first anchor portion 26A includes two splice points 36A, 36B, and the second anchor portion 26B includes two splice points 38A, 38B. The strand of suture 24 exits and re-enters the bore 34 through each of the splice points 36A, 36B, 38A, 38B. The distal-most and proximal-most splice points 36A, 38B are spaced inward of respective ends 30, 32 of the sheath 26. When the first and second anchor portions 26A, 26B are deployed adjacent soft tissue, tension is applied to the strand of suture 24, which cinches the first and second anchor portions 26A, 26B, anchoring them in place.

In the illustrated embodiment, the sheath 26 includes a central portion 27, which spans the entirety of the distance between the first and second anchor portions 26A, 26B. The sheath 26 covers the strand of suture 24 throughout the central portion 27. That is, there are no splice points between the first and second anchor portions 26A, 26B. As will be appreciated from the below discussion, the central portion 27 of the sheath 26 may be positioned on a surface of torn tissue, such as on the medial or inside surface of a meniscus. Therefore, this central portion 27 of the sheath 26 may be positioned adjacent the condyles of the knee, for example. In this way, the sheath 26 serves to protect the condyles of the knee from abrasion that may be caused by the strand of suture 24, which may include barbs.

Further, the sheath 26 also serves to prevent "tear through," which is when an implant tears through soft tissue. In the illustrated embodiment, the central portion 27 of the sheath 26 includes an increased width dimension $W_1$ relative to the remainder of the sheath 26, such as at locations adjacent the first or second anchor portions 26A, 26B, which have a relatively reduced width dimension $W_2$. In an embodiment, the sheath 26 is substantially circular in cross-section adjacent the first and second anchor portions 26A, 26B and is relatively flat or ovular in cross-section adjacent the central portion 27. The increased width dimension $W_1$ disperses the force applied by the strand of suture 24 over a relatively large surface area of soft tissue, which reduces the risk of "tear through."

The strand of suture 24 may be a monofilament suture. In order to keep the strand of suture 24 attached to the sheath 26, in one embodiment an end 40 of the strand of suture 24 is looped over and affixed to the strand of suture 24 adjacent one of the two splice points 36A, 36B of the first anchor portion 26A. In this example, the end 40 is passed through the first anchor portion 26A, and is bent back in the proximal direction and affixed to the strand of suture 24 at a location adjacent the splice point 36B. The end 40 may be affixed back to the strand of suture 24 by a knot or using some other fixation technique. The result is a loop 42 enclosing a portion of the first anchor portion 26A. The loop 42 retains the sheath 26 relative to the stand of suture 24 and ensures that the sheath 26 does not slide distally off the strand of suture 24.

The suture-implant construct 22 may be referred to as a "soft" construct because it is formed of soft materials such as yarns, fibers, filaments, strings, fibrils, strands, sutures, etc., or any combination of such materials. The soft materials may be synthetic or natural materials, or combinations of synthetic and natural materials, and may be biodegradable or non-biodegradable within the scope of this disclosure. In an embodiment, the suture-implant construct 22 is made exclusively of soft, suture-based materials. The soft materials confer the ability to be inserted into or through tissue (e.g., bone, ligament, tendon, cartilage, etc.) and then bunch together, collapse, expand, and/or change shape to fixate the suture-implant construct 22 relative to the tissue.

In an embodiment, the strand of suture 24 is provided by one of the following example types of suture: FiberWire®, TigerWire®, or FiberChain® suture, which are each available from Arthrex, Inc. It should be understood, however, that any type of suture may be used, including cored or coreless sutures. In another embodiment, the strand of suture 24 is flat suture, such as FiberTape® or SutureTape® suture, which is also available from Arthrex, Inc. The strand of suture 24 may also be a monofilament suture having barbs, as mentioned above. Further, the strand of suture 24 could include any soft, flexible strand of material, and is not limited to suture.

In an embodiment, the sheath 26 is a tubular sleeve made of a flexible material, such as a braided, woven, or knitted structure made of yarns, fibers, filaments, sutures, or other similar materials, or combinations of these materials. In another embodiment, the sheath 26 is constructed of polyester suture material. Other flexible materials may also be suitable for constructing the sheath 26.

FIG. 3 illustrates the arrangement between the cannula 14 and the pusher 18 from a top view (i.e., a superior view). As noted above, the cannula 14 is configured to penetrate soft tissue. To this end, the cannula 14 is tapered to a sharp, pointed distal end 44 in this example. The cannula 14 further includes a tubular bore 46, which receives the suture-implant construct 22 and the pusher 18. In this example, the cannula 14 further includes a slot 48 in a superior surface thereof. The slot 48 extends parallel to the longitudinal axis A of the cannula 14. The slot 48 includes opposing side walls 50, 52 which serve to guide movement of the pusher 18 in a direction parallel to the longitudinal axis A. The slot 48 may extend along a portion of the length of the cannula 14 or alternatively may extend along the entire length of the cannula 14.

The pusher 18 is configured to deploy a distal-most anchor portion of the suture-implant construct 22 and is also configured to move any additional anchor portions distally within the cannula. Specifically, in the example of the first and second anchor portions 26A, 26B, distal movement of the pusher 18 is configured to deploy the first anchor portion 26A and to move the second anchor portion 26B distally within the cannula 14 to a deploy position. A second distal movement of the pusher 18 will then deploy the second anchor portion 26B.

In one example, the pusher 18 includes a rod or shaft mechanically coupled to the trigger 16. The pusher 18 is configured to move in the distal and proximal directions in response to corresponding movement of the trigger 16. The pusher 18 further includes a blunt distal end 54 configured to push an implant in the distal direction. The distal end 54 in this example is a substantially planar surface arranged normal to the longitudinal axis A. The distal end 54 could be inclined at an acute angle relative to the longitudinal axis A. The pusher 18 further includes a relatively smooth superior surface 56, and relatively smooth side surfaces 58, 60 configured to slide relative to the respective side walls 50, 52 of the slot 48. The inferior surface 62 of the pusher 18 includes a shuttling rack 64 in this example, which is configured to interact with implants to move them distally within the cannula 14.

Figure 4:
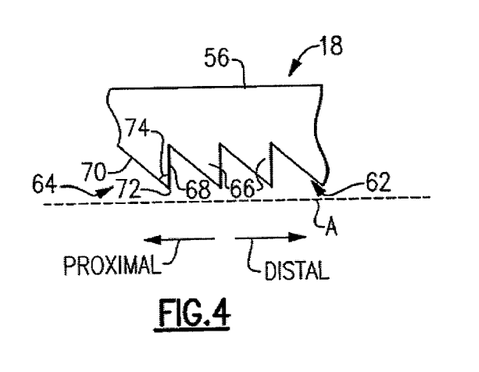
FIG. 4 is a side view illustrating a shuttling rack.

FIG. 4 illustrates the shuttling rack 64 in greater detail. In this example, the shuttling rack 64 is integrated into the pusher 18, meaning the shuttling rack 64 and pusher 18 are a single, integrated structure. The shuttling rack 64 includes a plurality of barbs 66 projecting from the inferior surface 62 of the pusher 18. The barbs 66 each include a distal face 68 and a proximal face 70. The distal and proximal faces 68, 70 meet at an apex 72, which provides a relatively sharp point and is configured to engage an anchor portion. In this example, the distal faces 68 are substantially normal to the distal direction and the longitudinal axis A, and the proximal faces 70 are inclined toward the proximal direction such that they project from the apex 72 at an acute angle 74 relative to the distal faces 68.

The shuttling rack 64 is configured to move anchor portions distally when the pusher 18 moves distally, and is also configured to not move anchor portions proximally as the pusher 18 moves proximally. Thus, during a sequence where the user U moves the trigger 16 in the distal direction and the trigger 16 moves back proximally under the bias of the spring, for example, the anchor portions within the cannula will only move in the distal direction.

Figure 5:
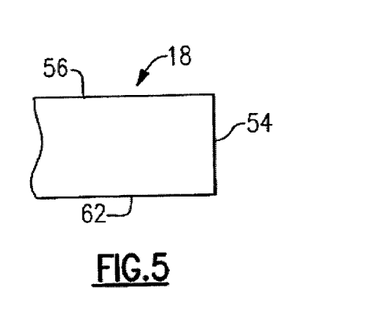
FIG. 5 is a side view illustrating the distal end of the pusher.

In this example, the pusher 18 does not include barbs 66 along the entirety of its length. Rather, as shown in FIG. 5, there is a section of the pusher 18 adjacent the distal end 54 where the inferior surface 62 is smooth. The inferior surface 62 may be smooth along a length corresponding to the length of the first and second anchor portions 26A, 26B. Alternatively, the inferior surface 62 may have barbs 66 along its entire length.

Figure 17:
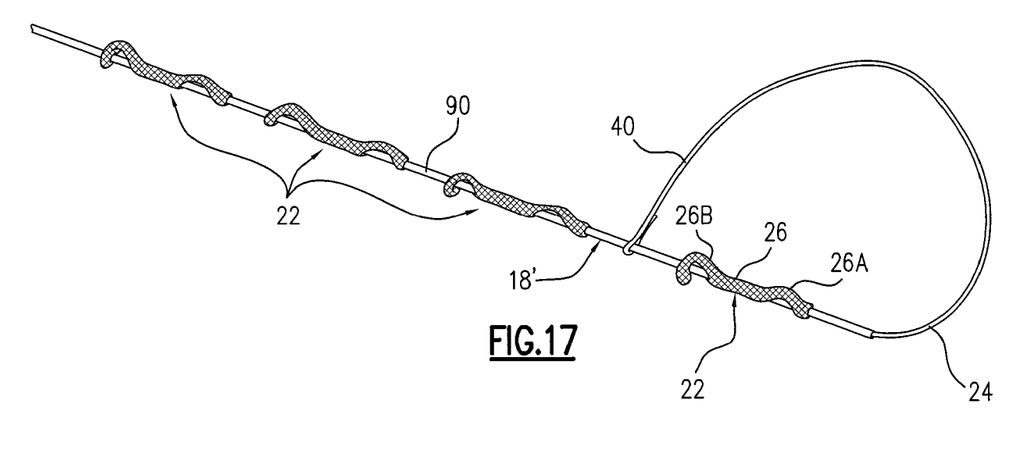
FIG. 17 is a perspective view of another surgical device loaded with a suture-implant construct that has more than one sheath.

In an alternative embodiment, the pusher 18' of the surgical device may be a holder tube 90 which extends through the bore 34 of one or more of the sheaths 26 via the splice points of each sheath 26, as best seen in FIG. 17. The sheaths 26 may be spaced apart from one another on the holder tube 90. The holder tube 90 and the sheaths 26 may reside in a cannula. The holder tube 90 is free to move back and forth relative to the sheaths 26. The sheaths 26 may be seated inside the cannula such that once the holder tube 90 moves behind the sheaths, the holder tube 90 will push the sheaths from behind. In this embodiment, the strand 24 may be extended or threaded through the holder tube 90 such that each sheath 26 may slide onto the strand 24 when the holder tube 90 is behind the sheaths, thereby deploying the first anchor portion 26A and any subsequent anchor portions of each sheath 26. The end 40 of the strand 24 may be affixed to the holder tube 90 in any known manner, such as a loop, a knot, or other fixation technique.

Figures 6, 8:
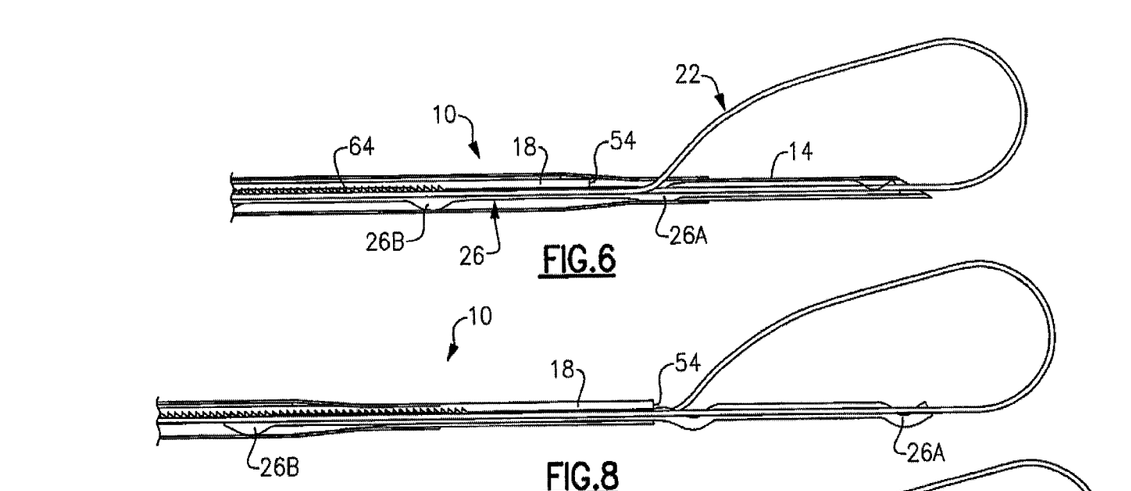
FIG. 6 is a cross-sectional view illustrating the surgical device with the entire suture-implant construct loaded into the cannula.
FIG. 8 is a cross-sectional view illustrating the surgical device with a first anchor portion deployed.

A method of using the surgical device 10 will now be described with reference to FIGS. 6-16. FIG. 6 is a cross-sectional view of the surgical device 10 and illustrates the surgical device 10 with the suture-implant construct 22 loaded into the cannula 14. In particular, the entire sheath 26, including each of the first and second anchor portions 26A, 26B, is positioned within the cannula 14. The distal end 54 of the pusher 18 is proximal to the first anchor portion 26A, and the shuttling rack 64 is contact with the second anchor portion 26B.

For purposes of this disclosure, the distal-most anchor portion within the cannula 14 is in a "deploy position" in which the implant is ready to be deployed by the pusher 18, and any remaining anchor portions are in a "standby position." The anchor portion in the standby position is essentially waiting to be moved to the deploy position and ultimately deployed by the pusher 18. In FIG. 6, the first anchor portion 26A is in the deploy position and the second anchor portion 26B is in a standby position.

Figure 7:
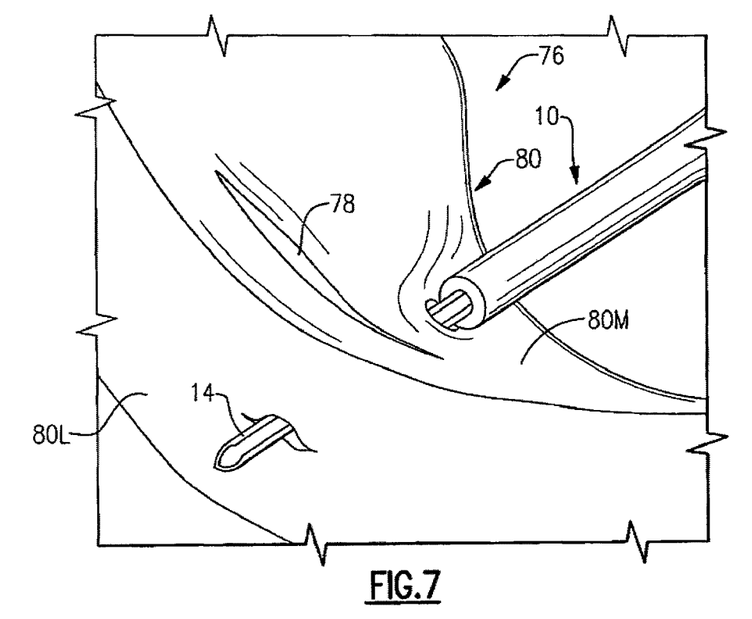
FIG. 7 is a view of the surgical device penetrating a meniscus in a first location adjacent a meniscus tear.

When in the position of FIG. 6, a user U can navigate the surgical device 10 within a joint space 76, as illustrated in FIG. 7. The joint space 76 in FIG. 7 is a joint cavity in a knee, and is specifically a cavity between a femur and a tibia. While a knee joint is illustrated, it should be understood that this disclosure extends to other joints. As illustrated in FIG. 7, there is a tear 78 in a meniscus 80. The meniscus includes a medial surface 80M, or interior surface, and a lateral surface 80L, or exterior surface. The surgical device 10 is used to deploy a plurality of implants in the area adjacent the tear 78 to close the tear 78 and allow it to heal.

Figure 9:
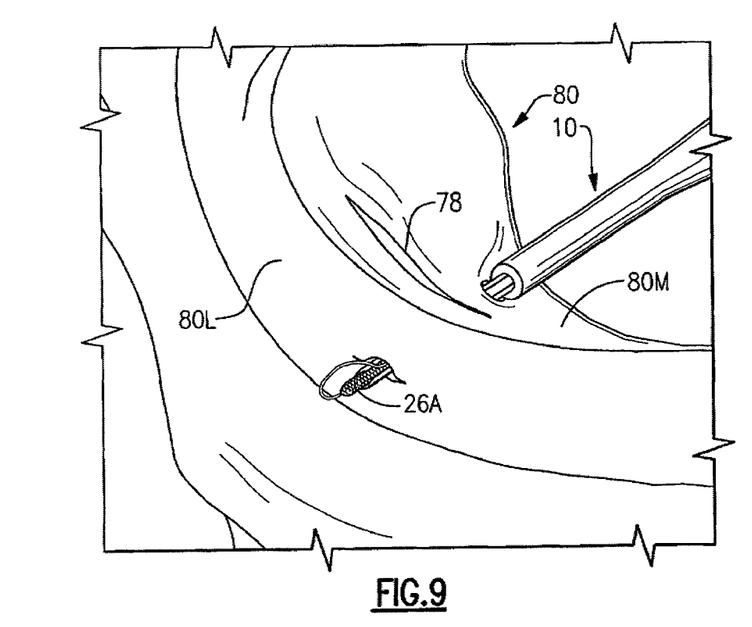
FIG. 9 is a view of the surgical device as the first anchor portion is deployed in the first location adjacent the meniscus tear.

In FIG. 7, a user U penetrates the cannula 14 through the meniscus 80 in a first location where the first anchor portion 26A is to be deployed. In particular, the user penetrates the cannula 14 into the medial surface 80M and out the lateral surface 80L. Alternatively, the user could penetrate the cannula 14 into the lateral surface 80L and out the medial surface 80M. When the cannula 14 is in the first location, the user U applies an input force to the trigger 16, which moves the pusher 18 distally. In FIG. 8, movement of the pusher 18 in the distal direction has deployed the first anchor portion 26A out of the cannula 14 and into a desired location adjacent the meniscus 80. FIG. 9 illustrates the first anchor portion 26A as it is being deployed in the first location adjacent the lateral surface 80L of the meniscus. Further, as shown in FIG. 8, the shuttling rack 64 has moved the second anchor portion 26B distally within the cannula relative to its position in FIG. 6.

Figures 10, 12:
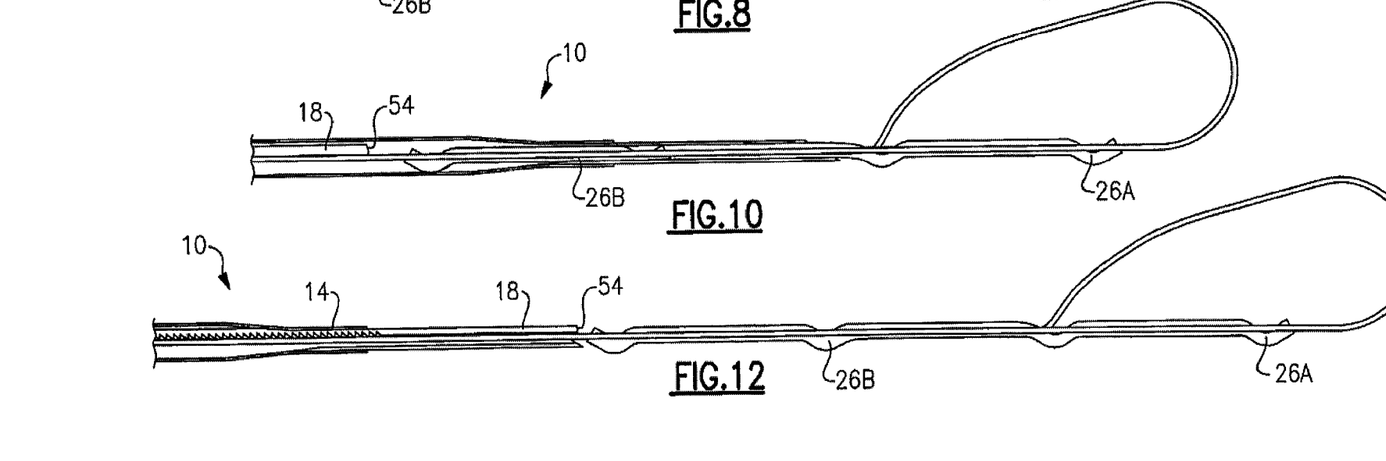
FIG. 10 is a cross-sectional view illustrating the surgical device with a second anchor portion moved to a deploy position.
FIG. 12 is a cross-sectional view illustrating the surgical device with the second anchor portion deployed.

After the first anchor portion 26A is deployed, the user U can remove their thumb, for example, from the trigger 16 allowing the trigger 16 and pusher 18 to move proximally to the position shown in FIG. 10. Again, proximal movement of the pusher 18 does not move the second anchor portion 26B proximally because of the arrangement of the shuttling rack 64, discussed above. In FIG. 10, the second anchor portion 26B has moved from a standby position (e.g., FIGS. 6, 8) to the deploy position (e.g., FIG. 10).

Figure 11:
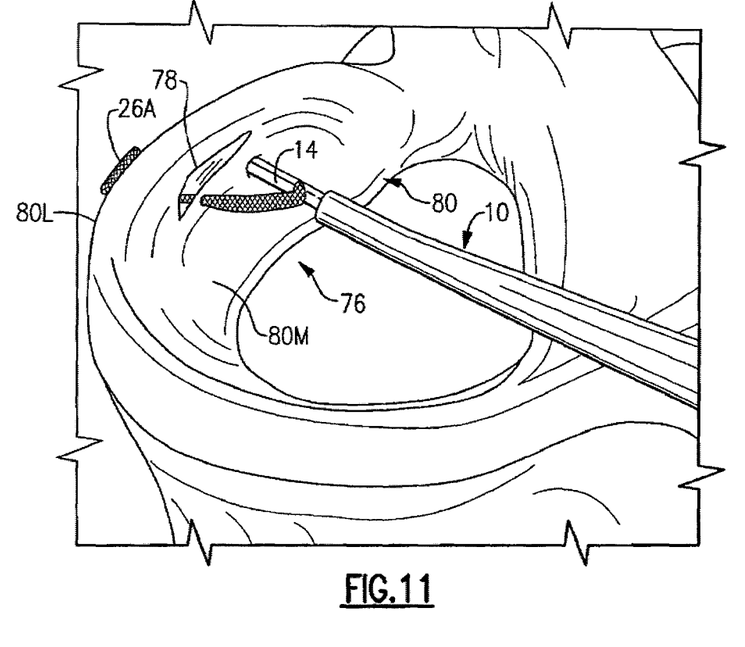
FIG. 11 is a view of the surgical device penetrating a meniscus in a second location adjacent the meniscus tear.
Figure 13:
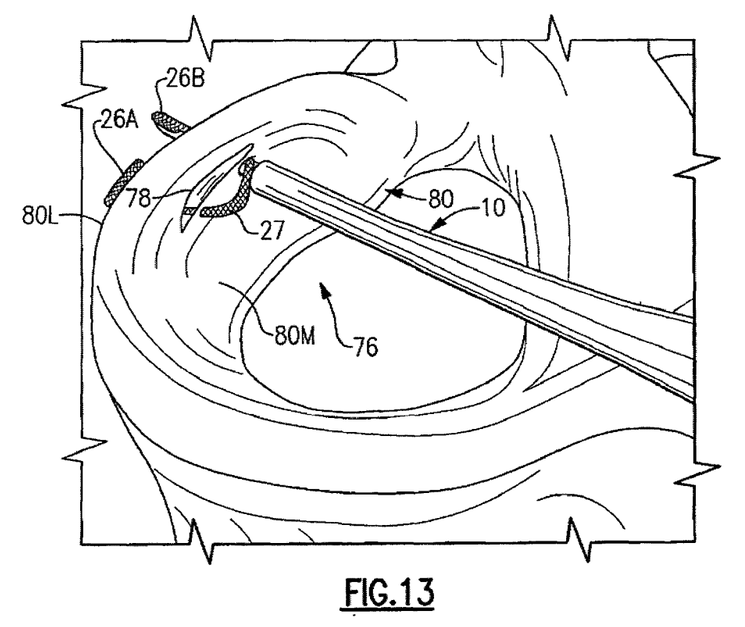
FIG. 13 is a view of the surgical device as the second anchor portion is deployed in the second location adjacent the meniscus tear.
Figure 14:
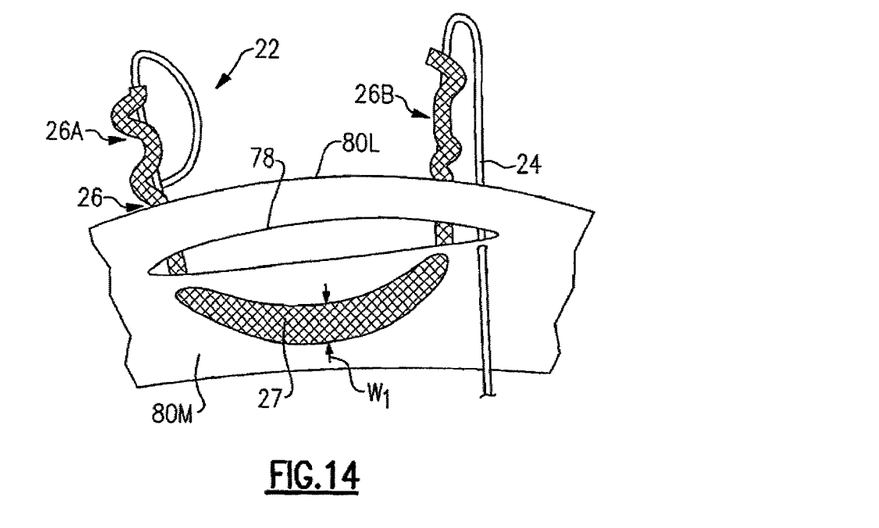
FIG. 14 is a top view of the suture-implant construct with the second anchor portion deployed in the second location.

When in the position of FIG. 10, the user U can position the cannula 14 in a second location adjacent the tear 78, as shown in FIG. 11. The second location is spaced-apart from the first location of FIG. 7. Once in the second location, the user U can penetrate the meniscus 80 and move the trigger 16 in the distal direction, which moves the pusher 18 in the distal direction, and deploys the second anchor portion 26B, as illustrated in FIG. 12. FIG. 13 illustrates the second anchor portion 26B as it is being deployed in the second location. FIG. 14 illustrates the suture-implant construct 22 after the second anchor portion 26B has been deployed from a top, or superior, view. As shown, the first and second anchor portions 26A, 26B are adjacent the lateral surface 80L of the meniscus 80, while the central portion 27 of the sheath spans between the first and second anchor portion 26A, 26B, including extending through the meniscus 80 and along the medial surface 80M adjacent the tear 78.

Figure 15:
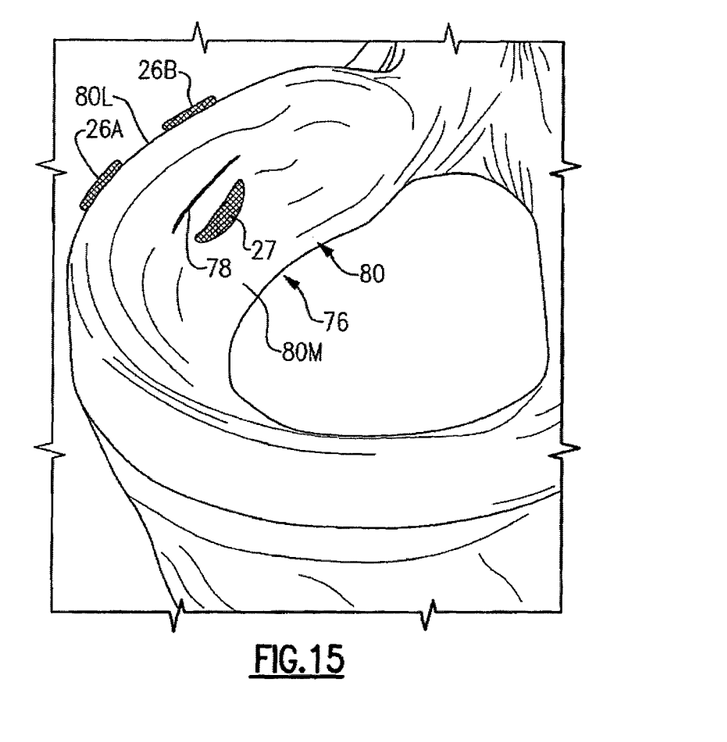
FIG. 15 is a view of a closed meniscus tear.

Once the first and second anchor portions 26A, 26B are deployed, the strand of suture 24 is tensioned. Doing so cinches or tensions the first and second anchor portions 26A, 26B such that the sheath 26 essentially bunches together and forms an anchor. Doing so also closes the tear 78, as generally shown in FIG. 15. The tensioned strand of suture 24 applies a force to the meniscus 80. The increased width dimension $W_1$ disperses that force over a relatively large area of the meniscus 80, which, as mentioned above, reduces the risk of "tear through."

While the suture-implant construct 22 includes two anchor portions 26A, 26B, additional anchor portions can be used to repair larger tears. In that case, the trigger 16 can be activated additional times to deploy each additional implant.

Figure 16:
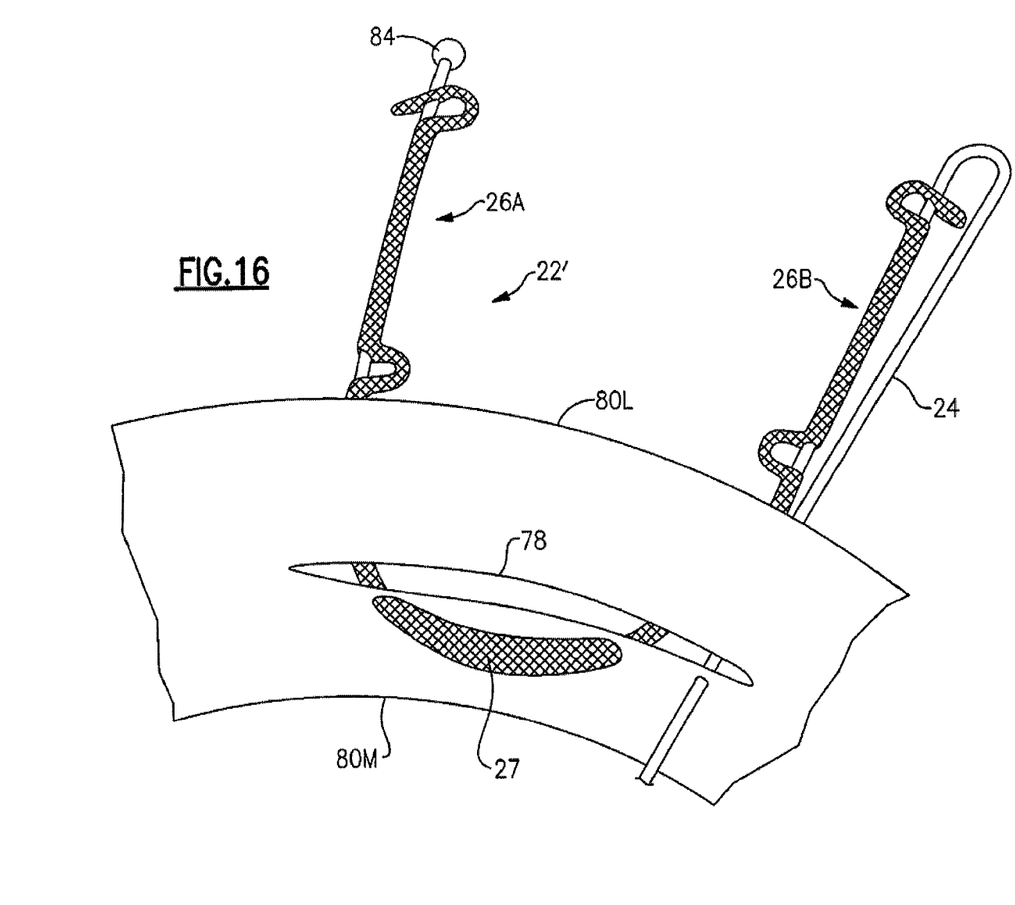
FIG. 16 is a top view of another suture-implant construct with the second anchor portion deployed in the second location.

While in FIG. 2 the strand of suture 24 is retained relative to the sheath 26 by being looped-back and affixed to itself, the strand of suture 24 could be retained in other ways. FIG. 16, for example, illustrates a suture-implant construct 22' arranged relative to a meniscus 80 in substantially the same way as FIG. 14. The strand of suture 24, in this embodiment, includes a bulb 84 at a distal end thereof. The bulb 84 has a diameter larger than the bore of the sheath 26, which prevents the sheath 26 from sliding distally off the strand of suture 24. While a loop (e.g., FIG. 2) and bulb (e.g., FIG. 16) have been shown, this disclosure extends to other techniques for retaining the strand of suture 24 relative to the sheath 26.

It should be understood that terms such as "lateral," "medial," "distal," "proximal," "superior," and "inferior" are used above consistent with the way those terms are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What we claim is:

1. A suture-implant construct, comprising:
   a flexible strand and one or more sheaths, each sheath comprising
   a) a first anchor portion,
   b) a second anchor portion spaced-apart from the first anchor portion, and
   c) an increased width dimension located between the first and second anchor portions, the increased width dimension has a width that is greater than a width of either of the first and second anchor portions.

2. The suture-implant construct as recited in claim 1, wherein:
   the sheath has a first end and a second end,
   the first anchor portion is adjacent to the first end of the sheath, and
   the second anchor portion is adjacent the second end of the sheath.

3. The suture-implant construct as recited in claim 2, wherein the flexible strand passes through a bore of the sheath between the first and second ends.

4. The suture-implant construct as recited in claim 3, wherein:
   the first anchor portion includes at least one splice point in which the flexible strand exits and re-enters the bore, and
   the second anchor portion includes at least one splice point in which the flexible strand exits and re-enters the bore.

5. The suture-implant construct as recited in claim 4, wherein:
   the first anchor portion includes two splice points spaced-apart from one another, and
   the second anchor portion includes two splice points spaced-apart from one another.

6. The suture-implant construct as recited in claim 5, wherein an end of the flexible strand is looped-over and affixed to the flexible strand adjacent one of the two splice points of the first anchor portion.

7. The suture-implant construct as recited in claim 2, wherein an end of the flexible strand includes a bulb adjacent the first end of the sheath.

8. The suture-implant construct as recited in claim 1, wherein the flexible strand is a suture.

9. The suture-implant construct as recited in claim 8, wherein the suture is a monofilament suture.

10. The suture-implant construct as recited in claim 8, wherein the sheath is a substantially tubular sleeve made of a flexible material.

11. The suture-implant construct as recited in claim 10, wherein the sheath is made of a polyester suture material.

12. The suture-implant construct as recited in claim 1, wherein each sheath is one-piece.

13. A suture-implant construct, comprising:
    a flexible strand and one or more sheaths, each sheath including,
    a) a first anchor portion,
    b) a second anchor portion spaced-apart from the first anchor portion, and
    c) a central portion located between the first and second anchor portions,
    wherein the first anchor portion is defined between first and second splice points spaced-apart from one another and the second anchor portion is defined between third and fourth splice points spaced-apart from one another, and a distance between the first and second splice points is substantially the same as a distance between the third and fourth splice points, and
    wherein the flexible strand passes through a bore of the sheath such that the flexible strand exits and re-enters the bore via the splice points of the first and second anchor portions.

14. The suture-implant construct as recited in claim 13, wherein the central portion is an increased width dimension of the sheath that has a width that is greater than the width of either of the first and second anchor portions.

15. The suture-implant construct as recited in claim 14, wherein the central portion spans the entirety of a distance between first and second portions.

16. A suture-implant construct, comprising:
    a flexible strand and one or more sheaths, each sheath having a first end and a second end, and each sheath including,
    a) a first anchor portion that is adjacent to the first end, and
    b) a second anchor portion spaced-apart from the first anchor portion, the second anchor portion being adjacent to the second end,
    wherein the flexible strand passes through a bore of the sheath between the first and second ends, the first anchor portion includes at least one splice point in which the flexible strand exits and re-enters the bore, and the second anchor portion includes at least one splice point in which the flexible strand exits and re-enters the bore,
    wherein the first anchor portion includes two splice points spaced-apart from one another, and the second anchor portion includes two splice points spaced-apart from one another, and
    wherein an end of the flexible strand is looped-over and affixed to the flexible strand adjacent one of the two splice points of the first anchor portion.

* * * * *